United States Patent [19]

Harris

[11] 4,102,937

[45] Jul. 25, 1978

[54] CYCLOPARAFFIN ISOMERIZATION USING A CATALYTICALLY ACTIVE ALUMINUM HALIDE INTERCALATED IN GRAPHITE

[75] Inventor: Jesse R. Harris, Bartlesville, Okla.

[73] Assignee: Phillips Petroleum Company, Bartlesville, Okla.

[21] Appl. No.: 747,126

[22] Filed: Dec. 3, 1976

[51] Int. Cl.$^2$ .............................................. C07C 5/28
[52] U.S. Cl. ..................... 260/666 P; 260/683.2; 252/441
[58] Field of Search .................... 252/441; 260/666 P, 260/683.2

[56] References Cited

U.S. PATENT DOCUMENTS

| | | | |
|---|---|---|---|
| 2,403,181 | 7/1946 | Jones | 260/683.5 |
| 3,285,990 | 11/1966 | Kelly | 260/683.7 |
| 3,785,999 | 1/1974 | Derleth | 252/441 |
| 3,925,495 | 12/1975 | Rodewald | 260/666 P |
| 3,962,133 | 6/1976 | Rodewald | 252/441 |
| 3,984,352 | 10/1976 | Rodewald | 252/441 |

OTHER PUBLICATIONS

R.C. Croft, Australian Journal of Chemistry, pp. 184–193, 1956.

*Primary Examiner*—Veronica O'Keefe

[57] ABSTRACT

The percentage conversion of isomerizable cycloparaffins is improved as compared to prior art methods by contacting the isomerizable cycloparaffins with a compound of aluminum halide intercalated in grahite and a hydrogen halide to form a catalytically active composition with a continuation of contact of the isomerizable cycloparaffins and the catalytically active composition to achieve substantial isomerization of the cycloparaffins.

9 Claims, No Drawings

CYCLOPARAFFIN ISOMERIZATION USING A CATALYTICALLY ACTIVE ALUMINUM HALIDE INTERCALATED IN GRAPHITE

BACKGROUND OF THE INVENTION

This invention relates to the isomerization of hydrocarbons. In one of its aspects this invention relates to isomerization of hydrocarbons using a compound of aluminum halide intercalated in graphite. In another of its aspects this invention relates to a composition of improved catalytic activity. In yet another of its aspects this invention relates to a method for preparing a catalytically active composition.

Up to the present, although it has been known to use aluminum halide intercalated in graphite as a catalyst for isomerization of hydrocarbons, the percent conversion to desired isomerization product has been sufficiently low to be considered commercially unacceptable. It has now been discovered that by contacting the hydrocarbon to be isomerized with an aluminum halide intercalated in graphite in the presence of a hydrogen halide that a composition of sufficient catalytic activity can be produced to give yields of isomerization product significantly improved over prior art methods.

It is therefore an object of this invention to provide a method for preparing a catalytically active composition for the isomerization of hydrocarbons. It is another object of this invention to provide a method for isomerizing hydrocarbons to yield good conversion rates to isomerization products. It is another object of this invention to provide a catalytically active composition of matter suitable as an isomerization catalyst.

Other aspects, objects and the various advantages of this invention will become apparent upon reading the specification and the attached claims.

STATEMENT OF THE INVENTION

According to this invention a method is provided for preparing a catalytic composition comprising contacting a compound of aluminum halide intercalated in graphite with a hydrogen halide in the presence of an isomerizable hydrocarbon for a time and at a temperature sufficient to form a catalytically active composition.

In a preferred embodiment of the invention a method for isomerizing hydrocarbons is provided in which isomerizable hydrocarbons are contacted with a compound of aluminum halide intercalated in graphite and a hydrogen halide for a time and at a temperature sufficient to form a catalytically active composition and the contact of the isomerizable hydrocarbon and the catalytically active composition is continued for a time and at a temperature and pressure sufficient to achieve substantial isomerization of the hydrocarbon.

The isomerizable hydrocarbons contemplated as feed in the process include linear or branched paraffins containing from about 4–8 carbon atoms per molecule, cycloparaffins containing from 5 to 6 carbon atoms in the ring and mixtures thereof. Particularly preferred classes of paraffins are cycloparaffins and alkyl-substituted derivatives thereof containing from 5 to about 12 carbon atoms per molecule. Exemplary compounds include n-butane, n-pentane, n-hexane, n-heptane, n-octane, 2-methylpentane, 3-methylheptane, methylcyclopentane, 1,2-dimethylcyclopentane, ethylcyclopentane, 1-ethyl-2-methylcyclohexane, methylcyclohexane, 1,2-di-n-propylcyclohexane, 1,2-dimethylcyclohexane, 1,4-dimethylcyclohexane and the like and mixtures thereof.

In carrying out the isomerization, contact between catalyst and hydrocarbon charge is usually conducted at a temperature ranging from about 0° C to about 300° C, preferably from about 0° C to about 200° C and usually at a pressure ranging from about 0 to about 1500 psia (6.9–10,340 kPa), preferably from about 0 to about 500 psia (6.9–3450 kPa), although higher temperatures and pressures can be used. It can readily be seen that the temperature and pressure are not critical as long as the feed is in the liquid state when contacted in the isomerization zone with the catalyst for a time sufficient to obtain a substantial amount of isomerization. For the purposes of this disclosure, "substantial amount" means at least 20 mole percent of the feed is isomerized. Contacting time can range from about 0.5 to 30 hours or more, preferably from about 2 to about 25 hours. The resulting product is removed from the reaction zone and separated into its components by any suitable means such as fractional distillation. Any unreacted starting material can be admixed with fresh material to form a feedstock for new runs.

The aluminum halide-graphite intercalation compounds are known compounds. They can be prepared, for example, as described by R. C. Croft, Australian Journal of Chemistry 9, 188–211 (1956) and in U.S. Pat. No. 3,925,495. Intercalation is generally achieved by heating a mixture of graphite and aluminum halide from about 1 to about 72 hours at a temperature ranging from about 80° C to about 300° C. Chlorine can be present during the reaction. The amount of aluminum halide intercalated in the graphite lattice ranges from about 2 to about 75 weight percent, preferably from about 5 to about 50 weight percent. The aluminum halide can be the fluoride, chloride, bromide or iodide. Aluminum chloride is presently preferred.

The isomerization activity of the aluminum halide/graphite intercalated compounds is increased by contacting a mixture of the catalyst and isomerizable hydrocarbon with a dry hydrogen halide for a period of time ranging from about 0.5 minute to about 60 minutes or more. Although higher temperatures can be used, contacting is usually carried out at a temperature in a range from about 0° C to about 300° C, preferably from about 10° C to about 100° C. It is presently preferred that the halogen atom of the aluminum halide and hydrogen halide be the same.

EXAMPLE I

The isomerization activity at room temperature was individually determined for a series of catalysts selected from among $AlCl_3$, graphite, and intercalated $AlCl_3$/graphite and HCl-promoted samples of these materials. The feedstock in each case was 8 cc of Phillips Research Grade methylcyclopentane. Analyses of the products were done by means of gas-liquid chromatography. Each catalyst and feed was charged to a 15 cc Diels-Alder tube under an argon atmosphere. The $AlCl_3$/graphite intercalate is a product of Alfa Inorganics and is described by them as containing about 35 wt. % $AlCl_3$.

The quantity of each catalyst used, the reaction time employed and results obtained are presented in Table I.

TABLE I
CATALYTIC ISOMERIZATION OF METHYLCYCLOPENTANE (MCP)

| Run No. | Catalyst Description | g | HCl Promotion Type | Temp. °C | Time Min. | Reaction Time, Hours | Product Analysis, Mole % Cyclohexane | MCP | MCP Conversion % | Comments | |
|---|---|---|---|---|---|---|---|---|---|---|---|
| 1 | graphite | 0.5 | none | — | — | 21 | 0 | 100 | 0 | control | |
| 2 | graphite | 0.5 | [a]invention | 25 | 5 | 2 | 0 | 100 | 0 | control | |
| 3 | AlCl$_3$ | 0.2 | none | — | — | 18.5 | 0 | 100 | 0 | control | |
| 4 | AlCl$_3$ | 0.2 | invention | 25 | 5 | 17.5 | 10.7 | 89.3 | 12 | control | |
| 5 | AlCl$_3$ | 0.2 | invention | 25 | 5 | 23.5 | 12.7 | 87.4 | 15 | control | |
| 6a | AlCl$_3$/graphite | 0.5 | [b]prior art | 100 | 300 | 1.5 | 0.7 | 99.3 | 0.7 | control | |
| 6b | AlCl$_3$/graphite | 0.5 | [b]prior art | 100 | 300 | 17.5 | 3.1 | 96.9 | 3.2 | control | |
| 6c | AlCl$_3$/graphite | 0.5 | [b]prior art | 100 | 300 | 20.0 | 3.2 | 96.8 | 3.3 | control | 1 hour run after fresh promotion |
| 6d | AlCl$_3$/graphite | 0.5 | invention | 25 | 5 | 21.0(1.0) | 4.0 | 96.0 | 4.2 | control | fresh promotion |
| 6e | AlCl$_3$/graphite | 0.5 | invention | 25 | 5 | 22.0(2.0) | 4.2 | 95.8 | 4.4 | control | 2 hour run after fresh promotion |
| 7a | AlCl$_3$/graphite | 0.5 | [c]prior art | 25 | 300 | 1.5 | 2.1 | 97.9 | 2.1 | control | |
| 7b | AlCl$_3$/graphite | 0.5 | [c]prior art | 25 | 300 | 17.5 | 5.9 | 94.1 | 6.3 | control | |
| 7c | AlCl$_3$/graphite | 0.5 | [c]prior art | 25 | 300 | 20.0 | 6.0 | 94.0 | 6.4 | control | |
| 7d | AlCl$_3$/graphite | 0.5 | [c]prior art | 25 | 300 | 25.0 | 6.0 | 94.0 | 6.4 | control | |
| 8a | AlCl$_3$/graphite | 0.5 | none | 25 | 300 | 19.0 | 7.0 | 93.0 | 7.5 | control | |
| 8b | AlCl$_3$/graphite | 0.5 | none | 25 | 300 | 24.0 | 10.5 | 89.5 | 12 | control | |
| 8c | AlCl$_3$/graphite | 0.5 | none | 25 | 300 | 42.0 | 13.0 | 87.0 | 15 | control | |
| 9a | AlCl$_3$/graphite | 0.5 | invention | 25 | 5 | 17.5 | 39.0 | 61.0 | 64 | invention | |
| 9b | AlCl$_3$/graphite | 0.5 | invention | 25 | 5 | 23.5 | 41.6 | 58.4 | 71 | invention | |

[a]HCL bubbled through reactant mixture.
[b]HCL passed over AlCl$_3$/graphite in a reactor at 5 GHSV as per U.S. Patent 3,925,495.
[c]After treatment, cooled to 25° C, purged with argon and stored in dry box under argon. Like b except treatment made at 25° C.

Inspection of the data in control runs 1–5 shows that graphite alone or AlCl$_3$ alone are not active isomerization catalysts in the process. Promotion of graphite with HCl also did not yield an active catalyst. Promotion of AlCl$_3$ with HCl according to the method used in the invention imparted modest activity to the catalyst. Control runs 8a–c show that the AlCl$_3$/graphite intercalate has roughly the same activity as a HCl-promoted AlCl$_3$ catalyst at comparable AlCl$_3$ levels. Activation of the intercalate according to control runs 6a–c and 7a–d by using a prior art procedure proved to be ineffectual as the results indicate. In addition, as control runs 6d–e show, bubbling HCl through the reaction mixture did not improve the activity of the catalyst very much.

Invention runs 9a–b clearly demonstrate that promotion of the AlCl$_3$/graphite intercalate in the presence of the isomerizable hydrocarbon as practiced in this invention yields an active catalyst for isomerization.

EXAMPLE II

Results in Example I raise a question as to whether an active catalyst for isomerization can be formed by treating the aluminum halide intercalated in graphite with a hydrocarbon other than the hydrocarbon that is isomerized and whether a hydrocarbon-catalyst mixture can be separated to give a catalyst mixture which, upon treatment with fresh hydrocarbon, would yield good conversion in the isomerization.

Experimental runs were carried out in the initiation stages using methylcyclopentane as activator with the addition of a second charge of methylcyclopentane to determine whether the second charge could be reacted over the active catalyst. Runs were then conducted using another hydrocarbon as activator and the methylcyclopentane as the second charge.

In all runs one-half gram of catalyst (aluminum chloride/graphite, 35–40 weight percent AlCl$_3$, from Alfa Inorganics) was mixed with 8 cc of methylcyclopentane and HCl was bubbled through the mixture for 5 minutes. This mixture was stirred for 1 hour and the methylcyclopentane was removed by syringe. A second charge of fresh methylcyclopentane, 8 cc, was injected and stirring was continued. The entire reaction was conducted at 26° C. The results are tabulated in Table II.

TABLE II

| Run | Activator | 2nd Charge | 20 hr. Con. (%) | Rate of reaction of 2nd charge (moles/hr/gr. cat) |
|---|---|---|---|---|
| 10a | MCP | — | 34.5 | 9.4×10$^{-3}$ |
| 10b | MCP | MCP | 15.5 | 3.7×10$^{-3}$ |
| 10c | MCP | MCP+HCl[1] | 21.5 | 5.2×10$^{-3}$ |
| 10d | MCP | MCP+HCl[2] | 24.0 | 8.0×10$^{-3}$ |
| 11a | 1-hexene | (Produced heavy oil) | | — |
| 11b | n-hexane | MCP+HCl[2] | 0 | — |
| 11c | cyclohexane | MCP+HCl[2] | 4 | — |

MCP=Methylcyclopentane
[1]=HCl bubbled through MCP for 5 minutes
[2]=HCL bubbled through MCP for 5 minutes in presence of catalyst These data show that the hydrocarbon to be isomerized should preferably be treated with the same hydrocarbon used as activator and as the isomerizable material. The data also show that it is preferable not to separate the activated catalyst mixture from the activating hydrocarbon, but to continue the isomerization in the original mixture. The conversion is approximately cut in half under conditions in which the hydrocarbon-catalyst mixture is separated and fresh hydrocarbon added, compare runs 10a and 10b. Runs 10c and 10d shows that the results of run 10b can be improved by treating the fresh hydrocarbon alone or in admixture with HCl at room temperature. These results suggest, as an alternative method for conducting the isomerization, the hydrocarbon-catalyst mixture can be separated, but if the separation is carried out, the fresh hydrocarbon added for the isomerization should be treated with hydrogen halide or the hydrocarbon in admixture with the catalyst should be treated with hydrogen halide.

Runs 11a, 11b, and 11c indicate that when methylcyclopentane is to be isomerized that methylcyclopentane should be used during activation of the catalyst.

By extrapolation of data it has been determined that using the same hydrocarbon in the activation and isomerization steps with no separation being made, the activation phase of the process is sufficiently complete in about 35 minutes and that isomerization can be detected. Activation is accomplished using an amount of about 0.005 moles of hydrocarbon per mole of intercalated aluminum halide for adsorption on the aluminum halide intercalated in graphite.

I claim:

1. A method for preparing a catalytic composition comprising contacting a compound of aluminum halide intercalated in graphite with a hydrogen halide in the presence in the liquid state of an isomerizable cycloparaffin for a time and at a temperature sufficient to form a composition catalytically active for isomerization of said cycloparaffin.

2. A composition catalytically active for isomerization of cycloparaffin said composition prepared by the method of claim 1.

3. A method for isomerizing cycloparaffin comprising:
    a contacting isomerizable cycloparaffin in the liquid state with a compound of aluminum halide intercalated in graphite and a hydrogen halide for a time and at a temperature sufficient to form a catalytically active composition; and
    b continuing contact of the isomerizable cycloparaffin and said catalytically active composition for a time and at a temperature and pressure sufficient to achieve substantial isomerization of the hydrocarbon.

4. A method of claim 3 wherein said time and temperature to promote catalytic activity is in the range of about 0.5 minutes to about 60 minutes and about 0° C to about 300° C, respectively.

5. A method of claim 3 wherein the halogen in the aluminum halide and the hydrogen halide is the same.

6. A method of claim 1 wherein said isomerizable cycloparaffin is chosen from among those containing from about 5 to about 6 carbon atoms in the ring and mixtures thereof.

7. A method of claim 6 wherein the isomerizable cycloparaffin is methylcyclopentane, the aluminum halide is $AlCl_3$, and the hydrogen halide is HCl.

8. A catalytically active composition prepared by the method of claim 6.

9. A method for isomerizing cycloparaffins according to claim 3 wherein said isomerizable cycloparaffins are chosen from among those containing from about 5 to about 6 carbon atoms in the ring and mixtures thereof.

* * * * *